United States Patent [19]

Osterried et al.

[11] Patent Number: 5,389,361
[45] Date of Patent: Feb. 14, 1995

[54] PRECURSOR PREPARATION FOR THE PRODUCTION OF NEUTRAL METAL OXIDE SOLS

[75] Inventors: Karl Osterried, Dieburg; Wolfgang Hechler, Lautertal-Reichenbach; Hans-Dieter Brückner, Darmstadt; Roland Martin, Weinheim, all of Germany

[73] Assignee: Merck Patent Gesellschaft mit beschrankter Haftung, Darmstadt, Germany

[21] Appl. No.: 898,586

[22] Filed: Jun. 15, 1992

[30] Foreign Application Priority Data

Jun. 14, 1991 [DE] Germany ............................ 4119719
Nov. 6, 1991 [DE] Germany ............................ 4136512

[51] Int. Cl.⁶ .......................... A61K 7/42; A61K 7/44; B01J 13/00
[52] U.S. Cl. .................................... 424/59; 252/62.56; 252/313.1; 252/313.2; 424/60; 514/943
[58] Field of Search ................. 252/313.1, 313.2, 610, 252/62.56; 424/59, 60; 514/943

[56] References Cited

U.S. PATENT DOCUMENTS

| | | | |
|---|---|---|---|
| 2,574,902 | 11/1951 | Bechtold et al. | 252/313.2 |
| 3,105,053 | 9/1963 | Cramer et al. | 252/313.1 |
| 3,440,174 | 4/1969 | Albrecht | 252/313.2 |
| 4,059,540 | 11/1977 | Crompton et al. | 252/309 |
| 4,322,400 | 3/1982 | Yuhas | 424/60 X |
| 4,472,510 | 9/1984 | January | 501/12 |
| 5,008,036 | 4/1991 | Crompton et al. | 252/313.1 |

FOREIGN PATENT DOCUMENTS 0154928 9/1985 European Pat. Off. .
0261560 9/1987 European Pat. Off. .

*Primary Examiner*—Richard D. Lovering
*Attorney, Agent, or Firm*—Millen, White, Zelano, & Branigan

[57] ABSTRACT

The invention relates to a preparation which is suitable for preparing a neutral metal oxide sol and contains 35–75% by weight of one or more metal oxide sols or metal oxide hydrates and 15–45% by weight of one or more hydroxycarboxylic acids and/or hydroxycarboxylic acid derivatives as stabilizers.

4 Claims, No Drawings

PRECURSOR PREPARATION FOR THE PRODUCTION OF NEUTRAL METAL OXIDE SOLS

BACKGROUND OF THE INVENTION

The invention relates to a preparation suitable for preparing a neutral metal oxide sol.

Neutral titanium dioxide sols and processes for their preparation are described, for example, in EP 0,261,560. According to this specification, an acid titanium dioxide sol is neutralized by treatment with an anion exchanger resin. During this procedure, the neutralized sol shows a tendency toward agglomeration, which can be counteracted by stirring the sol vigorously for several hours. Another possibility for avoiding agglomeration comprises adding a water-soluble organic compound to the sol before or after the treatment with the anion exchanger, monomeric or polymeric polyalcohols, such as, for example, glycerol, ethylene glycol or polyvinyl alcohol, being proposed in particular for this process in EP 0,261,560.

Neutral metal oxide sols are used in many instances in industry. Thus, for example, neutral metal oxide sols can be mixed with polymers or used as binders for certain catalysts. Because of their good skin tolerance and their high absorption in the UV range, neutral titanium dioxide sols have been proposed for cosmetic uses, and in particular for sunscreen cosmetics.

However, the neutral metal oxide sols described to date are often characterized by a storage stability which does not meet all requirements adequately. The metal oxide sols to date furthermore often have a relatively low concentration of typically not more than 10–25% by weight; thus, for example, a titanium dioxide sol of a maximum of about. 25% strength is obtained in EP 0,261,560 by heating a dilute neutral titanium dioxide sol. For many applications, such as, for example, for the preparation of cosmetics, however, more highly concentrated sols are desired.

SUMMARY OF THE INVENTION

One object of the present invention was to provide neutral metal oxide sols which have the disadvantages of conventional metal oxide sols to only a relatively small extent, if at all. Furthermore, a preparation which enables the user to prepare metal oxide sols in the particular desired concentration in a simple manner at any time was desired. Further objects of the present invention can be seen by the expert from the following detailed description and from the examples.

It has now been found that these objects can be achieved by providing the preparations according to the invention and the neutral metal oxide sols according to the invention.

The invention thus relates to a preparation which is suitable for preparing a neutral metal oxide sol and contains 35–75% of one or more metal oxides or metal oxide hydrates and 15–45% of one or more hydroxycarboxylic acids as a stabilizer.

The invention furthermore relates to a process for preparing such a preparation, characterized in that a metal oxide sol which is stabilized by one or more hydroxycarboxylic acids and has a pH of between 6 and 8 is freeze-dried.

The invention furthermore relates to a concentrated metal oxide sol obtainable by dissolving such a preparation in water or in an aqueous solution, and to the use of this metal oxide sol in cosmetic formulations.

The preparations according to the invention which are suitable for preparing a neutral metal oxide sol contain 3514 75% by weight, in particular 40–70% by weight and especially 50–60% by weight of one or more metal oxides or metal oxide hydrates respectively, which are preferably chosen from the group comprising titanium oxide, silicon oxide, chromium oxide, tin oxide, antimony oxide, zinc oxide, cobalt oxide, iron oxide, aluminium oxide and oxide hydrates thereof. Preparations which contain titanium dioxide, titanium oxide hydrate, iron oxide and/or iron oxide hydrate are especially preferred.

Further constituents of the preparations according to the invention are one or more hydroxycarboxylic acids or hydroxycarboxylic acid derivatives which function as stabilizers; citric and/or tartaric acid or derivatives derived from these acids are particularly suitable. The weight content of these stabilizers is between 15 and 45% by weight, in particular between 20 and 40% by weight and especially between 25 and 30% by weight.

The preparations according to the invention can additionally contain further constituents, such as, for example, salts formed by neutralization steps while the preparations are being prepared, such as, for example, NaCl, KCl, $Na_2SO_4$ etc., $H_2O$ or other further constituents.

The weight content of the further constituents in the preparations according to the invention is preferably not too high and in particular is not more than 30% by weight. Preparations in which the weight content of the further constituents is not more than 20% by weight and in particular less than 15% by weight are particularly preferred.

A metal oxide sol, which is prepared by processes which are known per se, is used to prepare the preparations according to the invention. An aqueous solution of an inorganic metal salt can thus be converted into the sol state, for example by hydrolysis, which can be effected, for example, by heating, and/or by acid peptization and/or by addition of a base or by other processes. Preferred processes for the preparation of titanium dioxide sol and iron oxide sol are described in Examples 1 and 2; sols of silicon oxide, chromium oxide, tin oxide, antimony oxide, zinc oxide, cobalt oxide, aluminium oxide and also other metal oxides can also be prepared analogously. However, the processes described in Examples 1 and 2 are to be understood as examples and are in no way intended to limit the invention.

The sol particles contained in the metal oxide sols used according to the invention typically have an average size of between 5 and 200 nm, and in particular between 5 and 100 nm. For purification, for example, the sol can be washed with distilled water or suitable salt solutions which do not lead to coagulation of the sol in a filtration plant, as is proposed in JP 63-48,358.

One or a mixture of several hydroxycarboxylic acids and/or hydroxycarboxylic acid derivatives is then added to the usually acid metal oxide sol, the ratio of the weight of the hydroxycarboxylic acids and/or hydroxycarboxylic acid derivatives added based on the metal oxide/oxide hydrate content of the starting material sol typically being between 0.2 and 1, preferably between 0.25 and 0.75 and in particular between 0.4 and 0.6. The hydroxycarboxylic acids can have from 1–6 hydroxy groups and 1–4 acid groups. The acids can contain aliphatic moieties, e.g., having 1–20 carbon atoms. In the aliphatic moieties, 1–4 double bonds can be present; however, saturated acids are preferred. Virtually any derivatives of these hydroxycarboxylic acids may be used in the invention. For example, alkali metal salts, alkaline earth metal salts, amine salts, mono-, di- and trialkylamides and esters may be used. Preferred hydroxycarboxylic acid derivatives are, for example, acid amides or salts of hydroxycarboxylic acids. Tartaric acid, citric acid and/or derivative thereof are especially preferred.

The mixture of metal oxide sol and one or more hydroxycarboxylic acids or derivatives thereof is then neutralized, neutral being understood here as a pH range of between 5.5 and 8.5, and in particular between 6 and 8. For this, a base, such as, for example, NaOH or KOH, is preferably added to the usually acid mixture of metal oxide sol and one or more hydroxycarboxylic acids. However, it is also possible, for example, for the anion of the inorganic or organic metal salt used to prepare the metal oxide sol to be removed from the mixture, for example with the aid of an anion exchanger, to change the pH.

It is also possible for the sequence of the two reaction steps just described—addition of one or more hydroxycarboxylic acids or derivatives thereof and neutralization—to be reversed. If the neutralization is carried out first, however, coagulation of the metal oxide sol is observed in most cases, which makes subsequent reaction with the carboxylic acid(s) and/or carboxylic acid derivative(s) more difficult, so that the above-mentioned sequence of reaction steps is preferred.

The neutral and very stable metal oxide sol obtained in this manner is used to prepare the preparations according to the invention, it being possible for different processes to be employed.

In a preferred process, for example, the neutral metal oxide sol is freeze-dried. The process is generally carried out between 1 and $10^{-3}$ mbar, and the drying times are typically between 2 and 30 hours.

In a different, also preferred process, the neutral metal oxide sol is spray-dried. Commercial spray-drying plants can be used; the inlet temperature is usually between 200° and 500° C. and, in particular, between 200° an 350° C., and the outlet temperature is typically between 50° and 300° C., and in particular, between 80° and 220° C.

The spray pressure is typically between 3 and 10 bar. The process conditions mentioned are understood as being exemplary and are intended to illustrate the invention without limiting it.

The preparations according to the invention are exceptionally stable to storage in air-tight and water vapor-tight packaging; in the case of photoactive preparations, such as, for example, in the case of preparations containing $TiO_2$, the use of packaging offering protection from light is also advisable.

The user can obtain metal oxide sols again by simple mixing of the preparations according to the invention with water or an aqueous solution, e.g., the aqueous phase of a desired cosmetic preparation and can easily vary their concentration within a wide range by the amount of water added. In addition to dilute metal oxide sols, highly concentrated metal oxide sols with a content of more than 30 or even more than 40% by weight solids, based on the total sol can thus be obtained.

The complete and simple solubility of the preparations according to the invention in water or aqueous solutions is surprising, since, for example, preparations obtained by freeze-drying acid titanium dioxide sols or acid titanium dioxide sols to which citric or tartaric acid has been added are only partly water-soluble, if at all. The preparations according to the invention have a lower transportation weight than metal oxide sols and are easy to handle. The metal oxide sols obtained by dissolving the preparations in water or aqueous solutions are exceptionally storage-stable; thus, for example, neutral sols stabilized by tartaric acid and/or citric acid thus have shelf lives of far more than 1 year. The properties of the metal oxide sols do not change as a result of the freeze-drying and the subsequent dissolving of the preparation in water or an aqueous solution; thus, for example, the value for the UV extinction of the titanium dioxide sol remains unaffected.

The metal oxide sols obtained by dissolving the preparations according to the invention can be used for diverse industrial and cosmetic applications. Use of the titanium dioxide sols prepared by dissolved $TiO_2$-containing preparations according to the invention in cosmetics is particularly preferred. The preparations according to the invention can be incorporated into cosmetic preparations or else non-cosmetic compositions or formulations, frequently also directly, which is preferred, without previous conversion into a sol being necessary. In addition to $TiO_2$-containing preparations, preparations containing iron oxide are also particularly preferred for cosmetic applications, since iron oxide has a UV extinction approximately $1\frac{1}{2}$ times that of titanium dioxide.

The metal oxide sols obtainable from preparations according to the invention meet the diverse requirements, especially in industrial or cosmetic applications, to a very much higher degree than metal oxide sols to date. The preparations according to the invention and the metal oxide sols obtainable therefrom are thus of considerable economic importance.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding applications German P 41 19 719, filed Jun. 14, 1991 and German P 41 36 512.7, filed Nov. 6, 1991, are hereby incorporated by reference.

EXAMPLE 1 a) Preparation of a titanium dioxide sol 1 l of completely demineralized water is brought to pH=1.5 by addition of 10% HCl at a temperature of 5° C. 250 ml of an aqueous $TiCl_4$ solution (400 g of $TiCl_4/l$) are then added at a metering rate of about 2 ml/min. and at a temperature of 3°–7° C., with vigorous stirring. The pH is kept at about pH=1.5 by simultaneous metered addition of an ion exchanger (Ion Exchanger II, commercial product of E. Merck, Darmstadt, Art. No. 4766, Hydroxyl Form). The mixture is subsequently filtered through a nylon filter (mesh width about 80 μm) to remove the ion exchanger. If appropriate, the filtrate can then also be subjected to extra fine filtration. An approximately 3–3.5% titanium dioxide sol is obtained. Titanium dioxide sols of 10–15% by weight can be obtained by evaporation using a rotary evaporator (about 30° C., pressure <20 mbar).

b) Preparation of a $TiO_2$-containing preparation according to the invention 200 g of a 12.6% by weight titanium dioxide sol which is obtained by the process described in a) are stirred with a solution of 12.6 g of citric acid in 13 ml of $H_2O$ at pH=1.5.

A white slurry is formed by this procedure, and is brought to pH=6.7 with 32% NaOH solution, while cooling with an ice-water bath; the white slurry becomes liquid as a result of the NaOH addition, and a transparent sol is obtained, which is freeze-dried under 0.1 mbar for 20 hours.

EXAMPLE 2 a) Preparation of an iron oxide sol 101.6 g of $FeCl_3 \cdot 6H_2O$ are dissolved in 570 ml of demineralized water, and 1.4 l of an ion exchanger (ion exchanger II, commercial product E. Merck, Darmstadt, Article No. 4766, hydroxyl form) are metered into the solution with vigorous stirring over the course of 3 hours at 3°–7° C.; after the ion exchanger has been added, the pH is 3.1.

The mixture is subsequently filtered through a nylon filter (mesh width about 80 μm) to remove the ion exchanger. A clear, dark brown iron oxide sol containing from about 2.5–4.5% by weight of $Fe_2O_3$ is obtained; the Cl ion content is 0.20% by weight. More highly concentrated iron oxide sols can also be obtained by evaporation using a rotary evaporator (conditions as in Example 1).

b) Preparation of an $Fe_2O_3$-containing preparation according to the invention 1.3 g of tartaric acid are added with stirring at pH 3 to 2 O g of a 1.3 % strength iron oxide sol obtained by the process described in a). During this addition, the pH drops to about 2, and the sol becomes cloudy and its viscosity increases; the pH is subsequently adjusted to 6.7 by dropwise addition of a 32% strength aqueous NaOH solution, and a clear sol is obtained which is freeze-dried at 0.1 mbar. The preparation prepared by this method is a brown powder.

In an example carried out analogously, the tartaric acid is replaced by citric acid.

EXAMPLE 3

A 10% strength neutral (pH=6.7) $TiO_2$ sol which has been stabilized with citric acid is prepared by the process described in Example 1 a), b). The sol is subsequently evaporated on a rotary evaporator to 10–25 mbar and 45°–60° C. until visible condensation on the condenser no longer takes place. A white powder of a residual water content of approximately 10–20% by weight is obtained.

EXAMPLE 4

A 9.3% strength neutral (pH=7) $TiO_2$ sol which has been stabilized with citric acid (4.65% by weight) is prepared by the process described in Example 1 a), b).

The sol is subsequently spray-dried in a spray-drying plant (transportable Minor Plant, Niro Atomizer) under the following (average) conditions:

| Inlet temperature $t_g$ [°C.] | Outlet temperature $t_A$ [°C.] | Spray pressure [bar] | Properties of the preparation obtained |
|---|---|---|---|
| 245 | 105 | 4.4 | fine, white powder water content 6.1% readily soluble in water |
| 220 | 100 | 4.4 | fine, white powder water content 5.7% readily soluble in water |
| 230 | 110 | 4.4 | fine, white powder water content 4.1% satisfactorily soluble in water |

EXAMPLE 5

To prepare a sun protection cream (o/w), phase A is heated to 75° C. and phase B to 80° C.

| | | % |
|---|---|---|
| A | glyceryl stearate (and) PEG-100 stearate | 10.00 |
| | mineral oil | 25.00 |
| | cetyl alcohol | 2.00 |
| | lanolin | 2.00 |
| | propylparaben | 0.05 |
| B | titanium dioxide preparation | to 5.00 $TiO_2$ |
| | glycerol | 2.00 |
| | sorbitol | 3.00 |
| | methylparaben | 0.15 |
| | demineralized water | to 100.00 |

Phase B is subsequently slowly stirred into phase A. The mixture is homogenized and allowed to cool to room temperature, with stirring. If desired, the cream can subsequently be perfumed at 45° C.

EXAMPLE 6

To prepare a sun protection cream (w/o), phase A is heated to 75° C. and phase B to 80° C.

| | | % |
|---|---|---|
| A | PEG-1 glyceryl oleostearate (and) paraffin wax | 6.00 |
| | mineral oil subliquidum | 14.50 |
| | beeswax | 3.00 |
| | caprylic/capric triglyceride | 11.00 |
| | dimethicone | 2.00 |
| | tocopherol acetate | 0.50 |
| | propylparaben | 0.05 |
| B | titanium dioxide preparation | to 5.00 $TiO_2$ |
| | glycerol | 2.00 |
| | methylparaben | 0.15 |
| | demineralized water | 10.30 |

Phase B is subsequently slowly stirred into phase A. The mixture is homogenized and allowed to cool to room temperature, with stirring. If desired, the cream can subsequently be perfumed at 45° C.

The sun protection cream has a viscosity of 38 000 mPas (Brookfield RVT, Sp. C, 10 rpm) at 24° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A water soluble neutral metal oxide sol comprising 35–75% by weight of at least one metal oxide sol or metal oxide hydrate sol and 15–45% by weight of at least one hydroxycarboxylic acid or water soluble salt or amide thereof, with the proviso that the metal oxide is not an antimony oxide.

2. In a cosmetic preparation or sunscreen comprising a metal oxide sol, the improvement wherein the sol is one of claim 1.

3. A water soluble neutral metal oxide sol comprising 35–75% by weight of at least one metal oxide sol or metal oxide hydrate sol and 15–45% by weight of at least one hydroxycarboxylic acid or water soluble salt or amide thereof, wherein the metal oxide is titanium oxide, silicon oxide, chromium oxide, tin oxide, zinc oxide, cobalt oxide, iron oxide or aluminum oxide.

4. In a cosmetic preparation or sunscreen comprising a metal oxide sol, the improvement wherein the sol is one of claim 3.

* * * * *